(12) United States Patent
Furman et al.

(10) Patent No.: US 10,232,090 B2
(45) Date of Patent: Mar. 19, 2019

(54) ELECTROPHORETICALLY DEPOSITED STRONTIUM FLUORIDE NANOPARTICLE/POLYMER COATINGS FOR MEDICAL IMPLANTS

(71) Applicant: Southwest Research Institute, San Antonio, TX (US)

(72) Inventors: Benjamin R. Furman, San Antonio, TX (US); Stephen T. Wellinghoff, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 32 days.

(21) Appl. No.: 13/974,814

(22) Filed: Aug. 23, 2013

(65) Prior Publication Data
US 2015/0056282 A1    Feb. 26, 2015

(51) Int. Cl.
*A61L 31/08*    (2006.01)
*C25D 13/04*    (2006.01)
(Continued)

(52) U.S. Cl.
CPC ............ *A61L 31/088* (2013.01); *A61K 33/16* (2013.01); *A61L 31/022* (2013.01); *A61L 31/10* (2013.01); *A61L 31/128* (2013.01); *C25D 13/00* (2013.01); *C25D 13/02* (2013.01); *C25D 13/04* (2013.01); *C25D 13/06* (2013.01); *A61L 2300/102* (2013.01); *A61L 2300/606* (2013.01); *A61L 2420/02* (2013.01); *A61L 2420/04* (2013.01); *A61L 2420/06* (2013.01)

(58) Field of Classification Search
CPC .... A61L 31/088; A61L 31/022; A61L 31/128; A61L 31/10; A61L 2420/04; A61L 2300/102; A61L 2420/02; A61L 2420/06; A61L 2300/606; C25D 13/04; C25D 13/06; C25D 13/02; C25D 13/00; A61K 33/16

See application file for complete search history.

(56) References Cited

U.S. PATENT DOCUMENTS 4,295,951 A * 10/1981 Bommaraju ............ C25B 11/00
                                                      204/242
4,425,467 A *  1/1984 Alvino .................... C08J 3/09
                                                      204/489
(Continued)

FOREIGN PATENT DOCUMENTS

EP          2266585 B1    6/2013
WO          2005089825    9/2005
WO      WO2013059745  *  4/2013  ............... A61F 2/02

OTHER PUBLICATIONS

Schwier et al. (Ozone oxidation of oleic acid surface film decreases aerosol cloud condensation nuclei activity, J. Phys. Resch. 2011, vol. 116, pp. 1-12).*

(Continued)

*Primary Examiner* — Trevor Love
(74) *Attorney, Agent, or Firm* — Grossman, Tucker et al

(57) ABSTRACT

The present disclosure provides for co-electrophoretic deposition (co-EPD) of organo-functionalized strontium fluoride nanoparticles ($SrF_2$) with a hydrophobic polymer in the presence of non-aqueous aprotic solvents. The co-EPD procedure can be employed to form a coating or self-supporting film for application to a metal implant.

11 Claims, 16 Drawing Sheets

(51) Int. Cl.

| | |
|---|---|
| C25D 13/06 | (2006.01) |
| C25D 13/02 | (2006.01) |
| C25D 13/00 | (2006.01) |
| A61L 31/02 | (2006.01) |
| A61L 31/12 | (2006.01) |
| A61K 33/16 | (2006.01) |
| A61L 31/10 | (2006.01) |

(56) References Cited

U.S. PATENT DOCUMENTS

| | | | |
|---|---|---|---|
| 5,433,718 | A | 7/1995 | Brinker |
| 5,824,048 | A | 10/1998 | Tuch |
| 5,876,743 | A * | 3/1999 | Ibsen et al. ............... 424/426 |
| 7,156,851 | B2 | 1/2007 | Christensen |
| 7,601,153 | B2 | 10/2009 | Shinjo et al. |
| 8,067,069 | B2 | 11/2011 | Li |
| 8,415,491 | B2 | 4/2013 | Furman et al. |
| 2004/0091605 | A1 | 5/2004 | Bayer et al. |
| 2005/0170071 | A1 | 8/2005 | Eramo |
| 2005/0220837 | A1 | 10/2005 | Disegi et al. |
| 2007/0078513 | A1 | 4/2007 | Campbell |
| 2008/0254125 | A1 | 10/2008 | Freier |
| 2008/0262630 | A1 | 10/2008 | Fulmer et al. |
| 2009/0181098 | A1 | 7/2009 | Garrett et al. |
| 2010/0042205 | A1 * | 2/2010 | Atanasoska et al. ........ 623/1.38 |
| 2010/0076569 | A1 * | 3/2010 | Langhorn ........... A61F 2/30767  623/22.21 |
| 2010/0331373 | A1 * | 12/2010 | Egashira ............ A61K 9/5153  514/342 |
| 2011/0217351 | A1 | 9/2011 | Cheng et al. |
| 2012/0006686 | A1 | 1/2012 | Furman et al. |
| 2012/0142954 | A1 | 6/2012 | Furman et al. |

OTHER PUBLICATIONS

Zhang et al. (solvothermal synthesis of well dispersed MF2 (M=Ca, Sr, Ba) nanocrystals and their optical properties, Nanotechnology, 2008, vol. 19, pp. 1-8).*

Powers (The electrophoretic forming of beta-alumina ceramic, J. Electrochem. Soc., 1975, vol. 122, pp. 490-498).*

Liu et al. (A review on fundamentals and applications of electrophoretic deposition (EPD), Progress in Material Science, 2007, vol. 52, pp. 1-61).*

Greenwoods, Review of the measurement of zeta potentials in concentrated aqueous suspensions using electroacoustics, Advances in colloid and interface science, 2003, vol. 106, p. 63.*

Pedroni et al., Water (H2O and D2O) dispersible NIR-to-NIR upconverting Yb3+/Tm3+ doped MF2 (M=Ca, Sr) colloids: influence of the host crystal, Crystal Growth Design, 2013, 13, p. 4906.*

Salopek et al., Measurement and application of zeta potential, Rudarsko-Geolosko-Naftino-Zbornik, 1992, vol. 4, pp. 147-151.*

As evidenced by Park et al. (Curcumin-loaded PLGA nanoparticles coating onto metal stent by electrophoretic deposition techniques, Bull Korean Chem. Soc., 2007, vol. 28, pp. 397-402).*

PKa table by Indiana University, 2016, p. 1.*

Cao et al., The first fluoride one-dimensional nanostructures: microemulsion-mediated hydrothermal synthesis of BaF2 whiskers, J. Am. Chem. Soc., 2003, vol. 125, p. 11196-11197 (Year: 2003).*

Encyclopaedia Brintannica, p. 1, https://www.britannica.com/science/dielectric, 2017, p. 1 (Year: 2017).*

Office Action dated Jun. 28, 2012 issued in related U.S. Appl. No. 12/717,666 (17 pgs).

Office Action dated Jan. 13, 2013 issued in related U.S. Appl. No. 12/717,666 (16 pgs).

Z.Chen, et al Versatile Synthesis Strategy for Carboxylic Acid-functionalized Upconverting Nanophosphors as Biological Labels; J. American Chemical Society 2008, vol. 130, No. 10, pp. 3023-3029.

B.Furman, et al "Electrophoretic Deposition of Organically Modified Gibbsite Nanocomposites With Liquid Crystalline Character", J. Mater Sci (2012) 47: pp. 6896-6907.

J.H.Gray, "Solubility Study of Strontium Fuel Compounds"; Martin Marietta Corporation, for U.S. Atomic Energy Commission, Contract AT (30-1) MND-3062-29 pp. (i-vi),(1-36).

P.L.Menezes, et al "Role of Surface Texture, Roughness, and Hardness on Friction During Unidirectional Sliding", Springer Science&Business Media, LLC2010, Tribological Lett., 2011; 41: pp. 1-15.

E. Pamula, et al., "Degradation, Bioactivity, and Osteogenic Potential of Composites Made of PLGA and Two Different Sol-Gel Bioactive Glasses", Annals of Biomedical Engineering, vol. 39, No. 8, Aug. 2011; pp. 2114-2129.

J-W Park, et al, "Positive Modulation of Osteogenesis and Osteoclastogenesis-Related Gene Expression With Strontium-Containing Microstructured Ti Implants in Rabbit Cancellous Bone", Journal of Biomedical Materials Research A, Jan. 2013, vol. 101A, Issue 1, pp. 298-306.

S Peng, et al.,The Cross-Talk Between Osteoclasts and Osteoblasts in Response to Strontium Treatment: Involvement of Osteoprotegerin, Elsevier / Bone, 2011; 49: pp. 1290-1298.

Z Saidak, et al, "Strontium Signaling: Molecular Mechanisms and Therapeutic Implications in Osteoporosis", Elsevier / Pharmacology and Therapeutics, 2012; 136: pp. 216-226.

D. Sales, et al., "Short-Term Fluoride and Cations Release From Polyacid-modified Composites in a Distilled Water and an Acidic Lactate Buffer", Elsevier Science, Biomaterials, 2003; 24: pp. 1687-1696.

J. Sun, et al., "Facile Synthesis of Well-dispersed SrF2:Yb+3/Er+3 Upconversion Nanocrystals in Oleate Complex Systems", Applied Surface Science, 2011; 257: pp. 3592-3595.

L. Zhou, et al "The Ostoeogenic Activity of Strontium Loaded Titania Nanotube Arrays on Titanium Substrates", Elsevier, Biomaterials, 2013, 34: pp. 19-29.

Adams, et al., "Controlled Release of Vancomycin from Thin Sol-Gel Films on Implant Surfaces Successfully Controls Osteomyelitis," Journal of orthopaedic research, 2009, vol. 27, No. 6, pp. 701-709.

Dejonge et al., "Organic-Inorganix Surface Modifications for Titanium Implant Surfaces," Pharm Res. Oct. 2008; 25 (10):2357-69.

Monjo et al., "In vivo performance of absorbable collagen sponges with rosuvastatin," Acta Biomaterialia vol. 6, Issue 4, Apr. 2010, pp. 1405-1412.

Bajpai et al., "Enhanced water sorption of a semi-interpenetrating polymer network (IPN) of poly(2-hydroxyethyl methacrylate)(PHEMA) and poly(ethylene glycol)(PEG)," Journal of Macromolecular Science, Part A, vol. 39, Issue 7 Jun. 2002, pp. 667-692.

Zhang et al., "Synthesis and solubility of (mono-)end-functionalized poly(2-hydroxyethylmethacrylate-g-ethylene glycol) graft copolymers with varying macromolecular architectures," Macromolecules, 2005, 38 (6), pp. 2530-2534.

Casimiro, et al., "Drug release assays from new chitosan/pHEMA membranes obtained by gamma irradiation," Nuclear Instruments and Methods in Physics Research Section B: Beam Interactions with Materials and Atoms vol. 265, Issue 1, Dec. 2007, pp. 406-409.

Weaver, et al., "Stimulous-Responsive Water-Soluble Polymers Based on 2-Hydroxyethyl Methacrylate," Macromolecules 2004, 37, 2395-2403.

Meinig, "Clinical Use of Resorbable Polymeric Membranes in the Treatment of Bone Defects," Orthopedic Clinics of North America—vol. 41, Issue 1 (Jan. 2010) pp. 39-47.

Patel, et al., "Physicochemical Characterization and Dissolution Study of Solid Dispersions of Lovastatin with Polyethylene Glycol 4000 and Polyvinylpyrrolidone K30," Pharmaceutical Development and Technology, vol. 12, Issue 1 Jan. 2007 , pp. 21-33.

Greene, et al., "Chitosan-coated Stainless Steel Screws for Fixation in Contaminated Fractures," Clinical Orthopaedics and Related Research vol. 466, No. 7; Jul. 2008, pp. 1699-1704.

Hermanson, Greg T. "5-Heterobifunctional Cross-linkers, Bioconjugate Techniques", Academic Press, San Diego, 1996, pp. 228-286, ISBN

(56) References Cited

OTHER PUBLICATIONS 9780123423351, 10. 1016/B978-012342335-1/50006-3. (http://www.sciencedirect.com/science/article/pil/b9780123423351500063).

\* cited by examiner

ELECTROPHORETICALLY DEPOSITED STRONTIUM FLUORIDE NANOPARTICLE/POLYMER COATINGS FOR MEDICAL IMPLANTS

GOVERNMENT FUNDING

This invention was made with United States Government support under Contact Award No. W81XWH-11-2-0128/ AGMTDTD091511 awarded by the U.S. Army Medical Research Acquisition Activity. The Government has certain rights in this invention.

FIELD OF THE INVENTION

This disclosure relates to electrophoretic deposition of strontium fluoride nanoparticle/polymer coatings and self-supporting films for medical devices. The coatings are bioactive and provide wound healing benefits.

BACKGROUND

Medical devices such as intramedullary (IM) rods may include a biocompatible coating (film) applied thereto for controlled release of an included medicament, such as antibiotics (e.g. vancomycin) and anabolic agents (e.g. statin). Biocompatible coatings may further include a polymer matrix for the medicament that will bioresorb over time, such as chitosan or collagen.

Simple solvent casting of the medicament/polymer matrix composite may be utilized to provide a biocompatible coating, but such may be impractical based on the topologically complex surfaces of many medical devices (e.g. curved, grooved rods and plates with through holes for screws, etc.).

Alternatively, electrophoretic deposition (EPD) from aqueous systems may be used to deposit the matrix on a topologically complex surface of the device, however, such may suffer from the production of hydrogen gas bubbles at the anode, i.e. the metallic substrate of the medical device (e.g. titanium (Ti), magnesium (Mg), or stainless steel (SS)) which may disrupt coating integrity.

However, in many situations the medicament and/or supporting polymer matrix are not water, but rather organo-soluble. In such situation, an organic solvent may be used in the electrophoretic deposition which will include aprotic organic solvents (e.g. tetrahydrofuran, methyltetrahydrofuran, methylene chloride). For example, bioresorbing polymers such as poly(d,l lactide-glycolide) (PLGA), poly(1-lactide) (PLLA) and polycaprolactone (PCL) are not water soluble at any pH, unlike other resorbing polymers, such as chitosan, which is water soluble at a pH of less than 6.

Certain inorganic nanoparticles themselves may act as medicaments for specific biomedical purposes. For example, strontium ion ($Sr^{+2}$) exhibits anabolic/anticatabolic action useful for bone defect and fracture repair. Nanoparticles containing strontium (Sr) have been formed directly on an anodized titanium (Ti) surface (titanium dioxide ($TiO_2$)) by hydrothermally treating after exposure to strontium ion ($Sr^{+2}$) solutions to form $SrTiO_3$.

SUMMARY

In one embodiment, the present disclosure is directed at a method for forming a $SrF_2$ nanoparticle/polymer coating or self-supporting film on a metallic substrate. The method begins by supplying nanoparticles of $SrF_2$ capable of providing $Sr^{2+}$ ions wherein the particles have a largest linear dimension of 20 nm to 10.0 µm and a thickness of 1 nm to 200 nm wherein said particles have a zeta potential of −20 to −50 mV. This is then followed by supplying a hydrophobic polymer containing functionality capable of associating with the $Sr^{2+}$ ions and forming an ionic association between the hydrophobic polymer and the $Sr^{2+}$ ions. The $SrF_2$ nanoparticles associated with the hydrophobic polymer are then placed in an aprotic solvent and one applies a potential and deposits a coating or self-supporting film containing $SrF_2$ particles associated with the hydrophobic polymer on a metallic substrate.

In product form, the present disclosure relates to a coating or self-supporting film applied to a metallic substrate for implantation in a human or animal comprising nanoparticles of $SrF_2$ that provide $Sr^{2+}$ ions wherein the particles again have a largest linear dimension of 20 nm to 10.0 µm and a thickness of 1 nm to 200 nm and a zeta potential of −20 to −50 mV. The hydrophobic polymer contains functionality that forms an ionic association between the hydrophobic polymer and the $Sr^{2+}$ ions.

FIGURES

The above-mentioned and other features of this disclosure, and the manner of attaining them, will become more apparent and better understood by reference to the following description of embodiments described herein taken in conjunction with the accompanying drawings, wherein.

Figure 12:
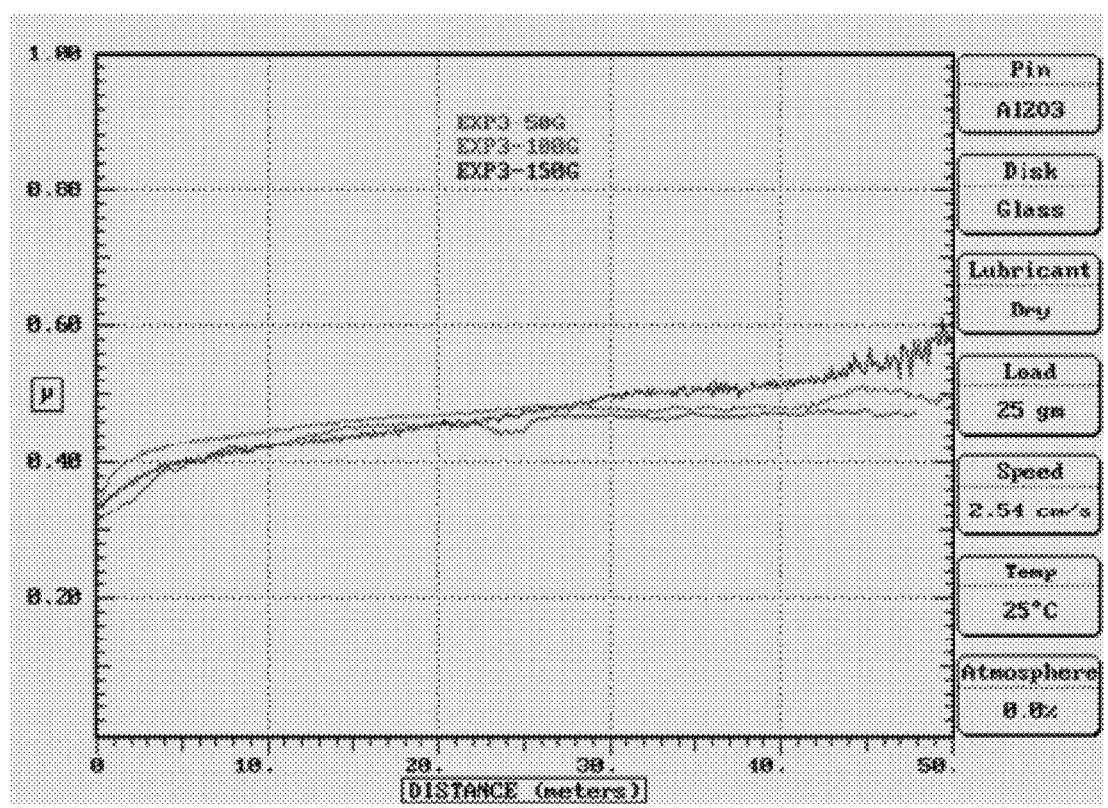
Figure 12A:
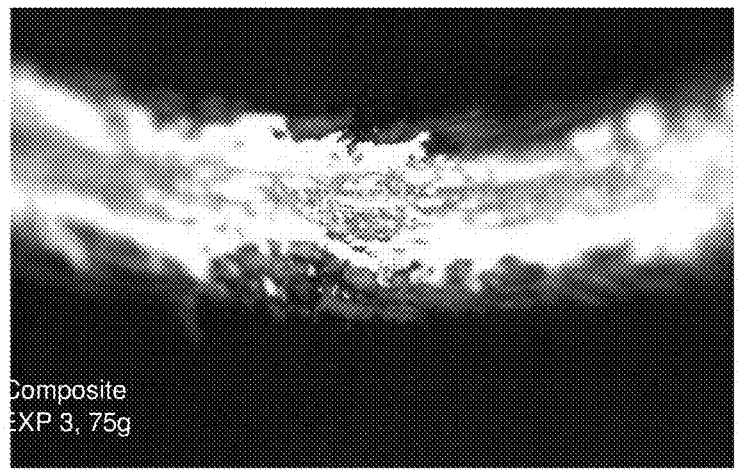
Figure 12B:
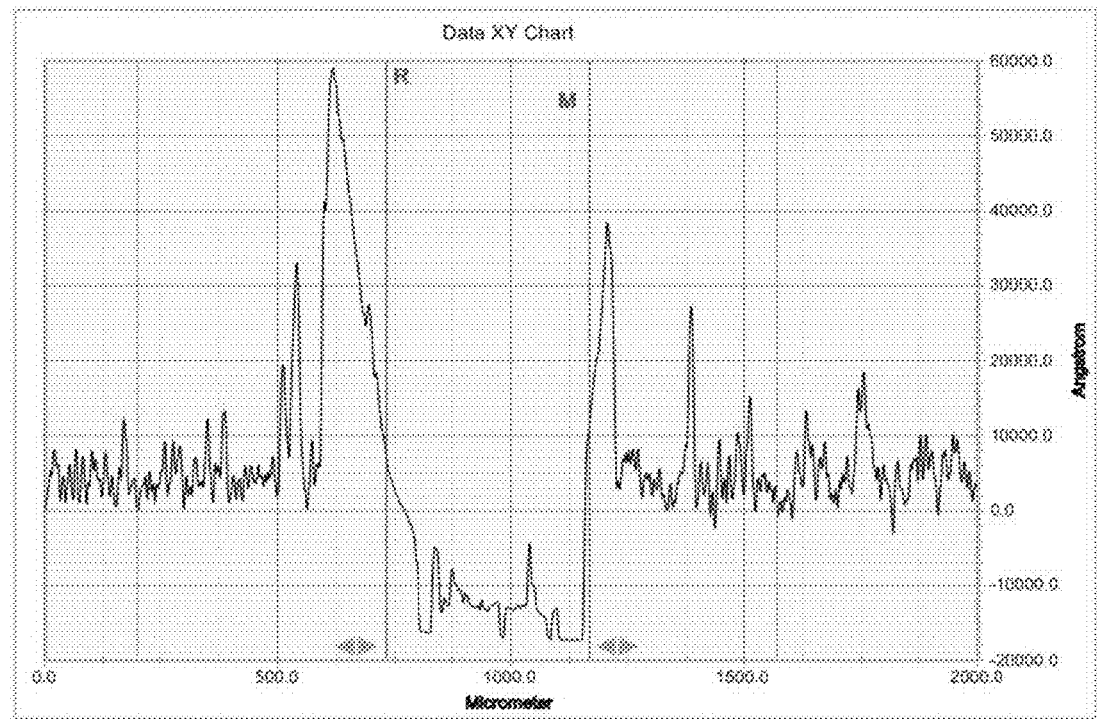
Figure 13A:
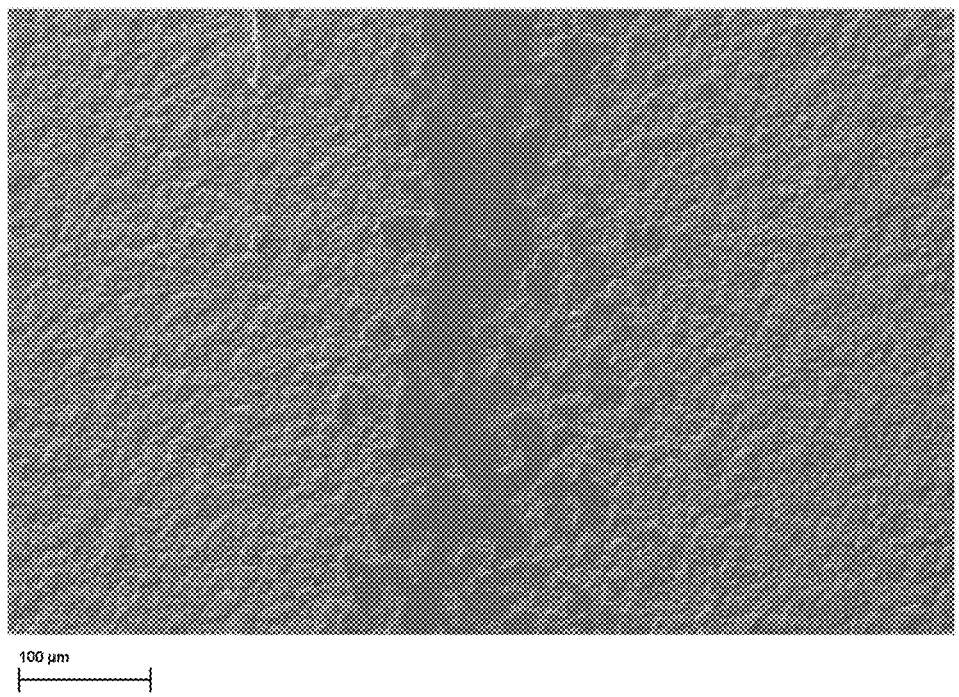
Figure 13B:
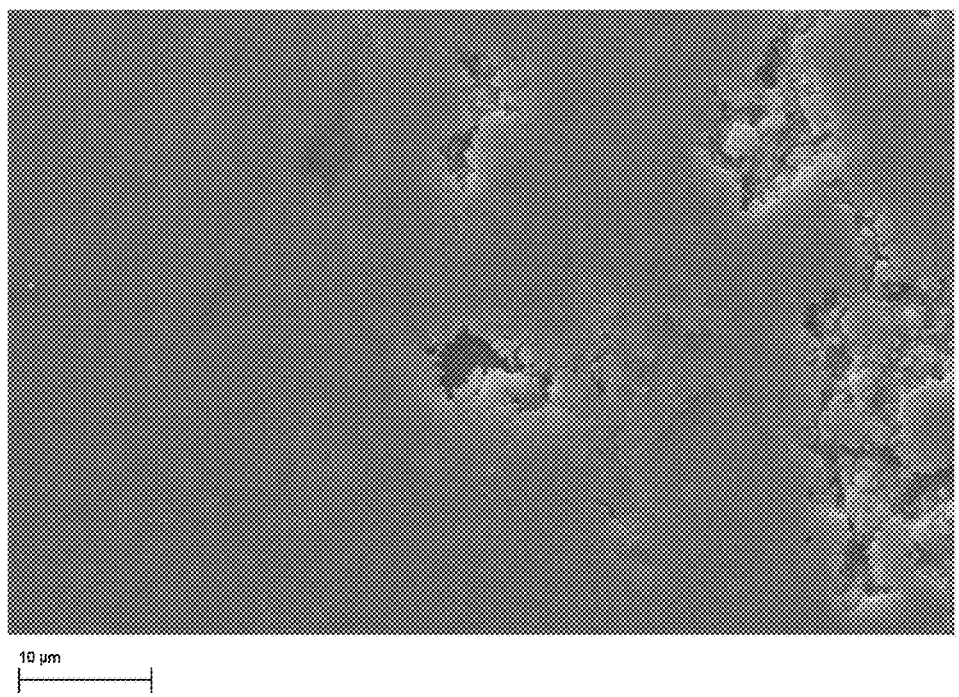
Figure 14A:
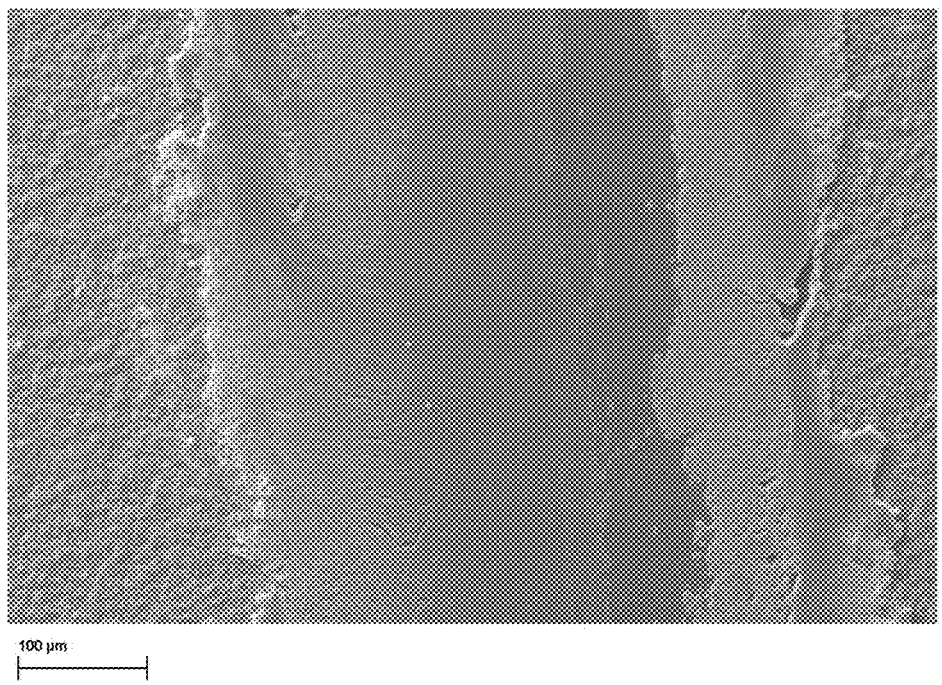
Figure 14B:
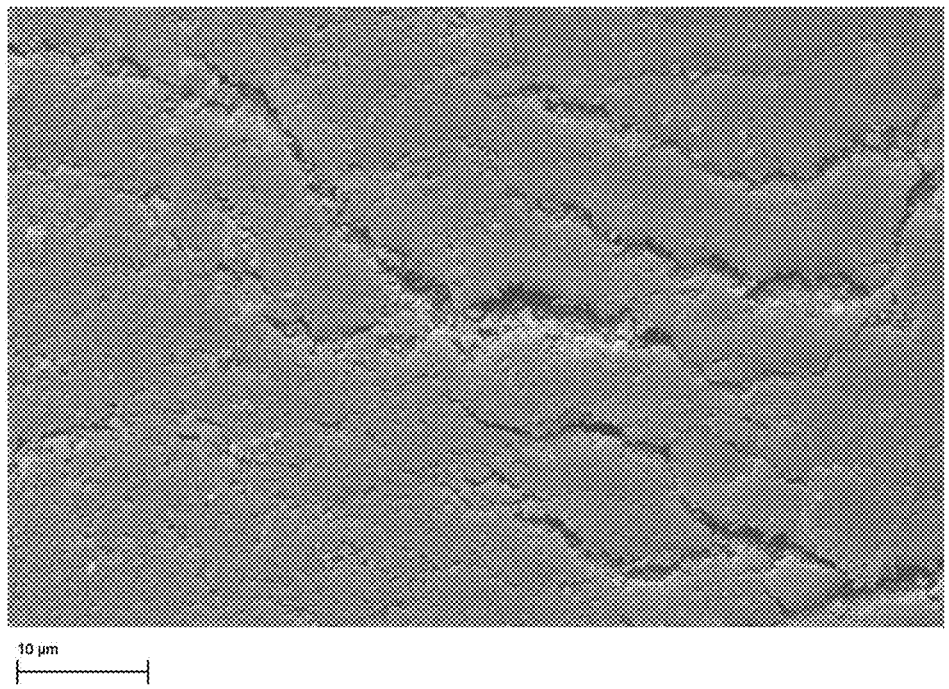
Figure 15A:
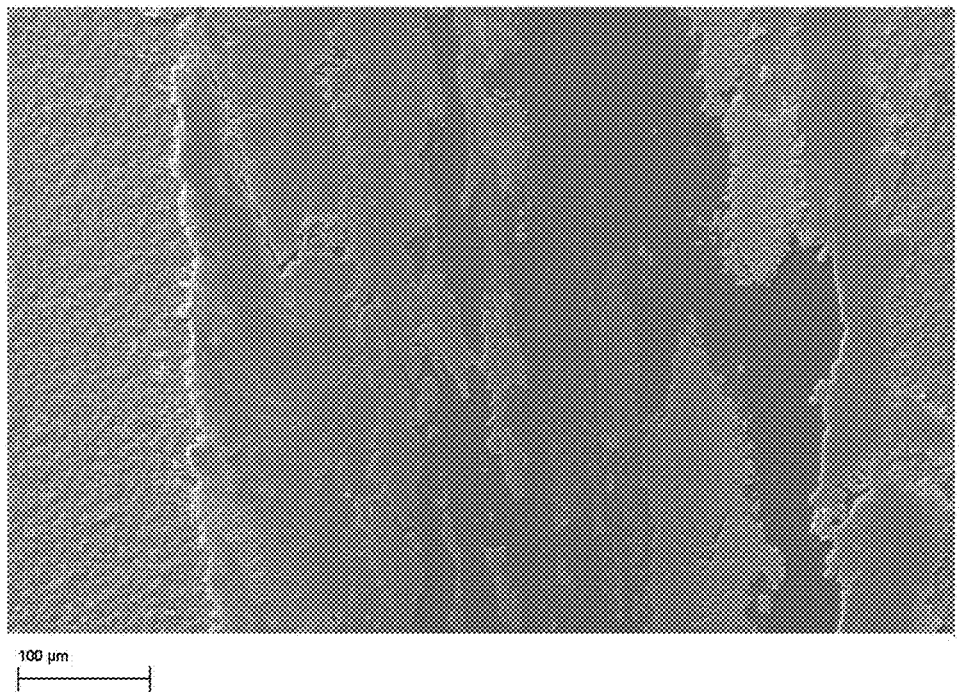
Figure 15B:
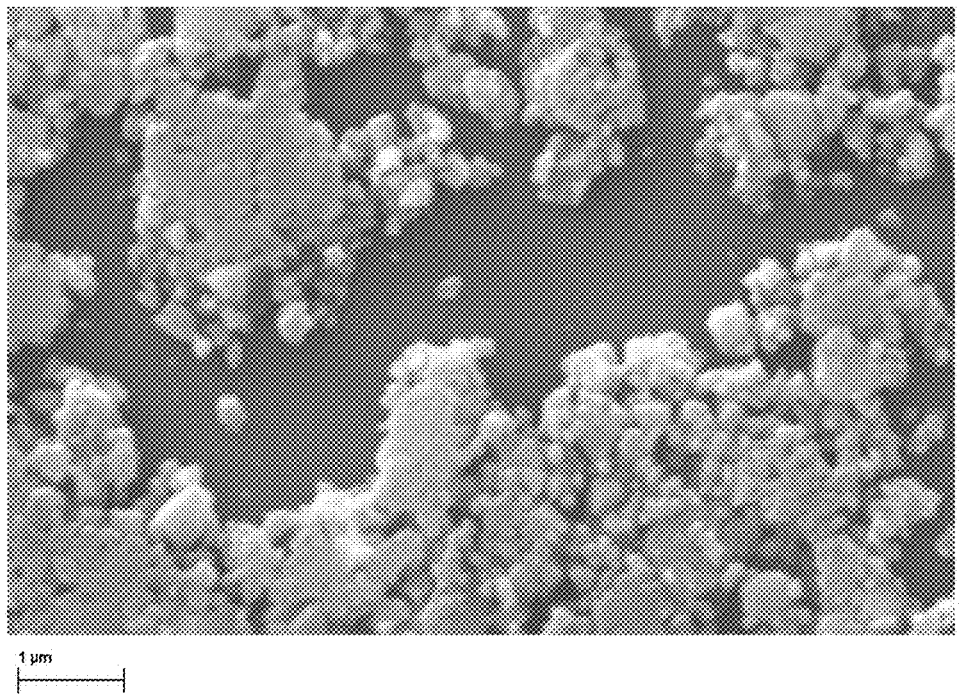

FIG. 12 is a coefficient of friction, μ, vs distance plot along the circular path of the pin on the test apparatus of FIG. 10A. The applied loads are ½ the values of the weights listed in the insert. Thickness and composition of composite film the same as in FIGS. 7 and 8;

FIG. 12A is a profilometer image and FIG. 12B is a wear track for the composite film of FIG. 12 showing the track for 75 g load at the completion of the experiment (50 meters);

FIG. 13A shows the track for 25 g load (inner track) at low magnification while FIG. 13B shows the track for 25 g load (inner track) at high magnification;

FIG. 14A shows the track for 50 g load (middle track) at low magnification while FIG. 14B shows the track for 50 g load (middle track) at high magnification;

FIG. 15A shows the track for 75 g load (outer track) at low magnification while FIG. 15B shows the track for 75 g load (outer track) at high magnification;

DETAILED DESCRIPTION

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

The present disclosure provides for co-electrophoretic deposition (co-EPD) of organo-functionalized strontium fluoride nanoparticles ($SrF_2$) with a hydrophobic polymer in the presence of non-aqueous aprotic solvents. The co-EPD can be employed to form a coating or self-supporting film for application to a metal implant. The polarity (zeta potential) of the $SrF_2$ nanoparticles may be adjusted and the co-EPD process may be selectively configured to generate a desired $SrF_2$ nanoparticle/hydrophobic polymer ratio.

Strontium fluoride ($SrF_2$) nanoparticles can be prepared herein by hydrothermal synthesis. Such synthesis may be understood as crystallization of the $SrF_2$ from relatively high temperature solution at relatively high vapor pressures. The $SrF_2$ particles so produced may have a size range (largest linear dimension through any portion of the particle) of 20 nm to 10.0 μm with a thickness of 1 nm to 200 nm, including all individual sizes and ranges therein in 1 nm increments. Accordingly, the size range (largest linear dimension) may be from 21 nm to 10.0 μm or 22 nm (largest linear dimension) to 10.0 μm, etc. The thickness may be from 2 nm to 200 nm or 3 nm to 200 nm, etc. One preferred size is 180-220 nm (largest linear dimension) at a thickness of 4-6 nm. The nanoparticles may be in the form of platelets that may be square or rectangular in their lateral proportions with a maximum size of 10.0 μm in any orthogonal direction with respect to the platelet edges. In general, aspect ratios, 1/d, of at least 10 are preferred for reinforcement of the polymer phase.

Figure 1:
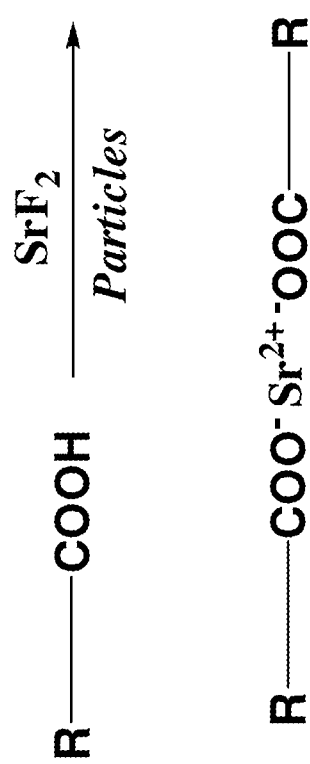
FIG. 1 illustrates the general functionalization of $SrF_2$ via association of the $Sr^{+2}$ ion with a carboxylate anion of a carboxylic acid.

The $SrF_2$ particles may be functionalized, which is in reference to the feature of modifying the zeta potential (ζ-potential) of the particles to permit the formation of a dispersion of the particles in non-aqueous solvents for electrophoretic deposition in the presence of a hydrophobic polymer. The ζ-potential of the $SrF_2$ particles may therefore have a value of −20 to −50 mV as measured in acetonitrile in a ZetaPALS 90 Plus instrument, available from Brookhaven instrument Corporation, using a standard potential of 20 V, a field frequency of 2 Hz, and seven repetitions. A preferable ζ-potential of the $SrF_2$ particles falls in the range of −24 to −26 mV. The above referenced functionalization of the $SrF_2$ particles is reference to the preferred feature of complexing the $SrF_2$ particles with a carboxylate ligand. For example, as illustrated in FIG. 1, one may generally utilize a monofunctional carboxylic acid which may then complex with the $Sr^{2+}$ through the indicated carboxylate anion. However, it may be appreciated that other suitable functional groups may be employed which will afford suitable functionality to ionically associate with $Sr^{2+}$, such as thiol, alcohol or hydroxyl, and alkoxy functionality (capable of providing $S^-$, $O^-$, or —Ö—). It is also contemplated that one may utilize ester groups.

Figure 2:
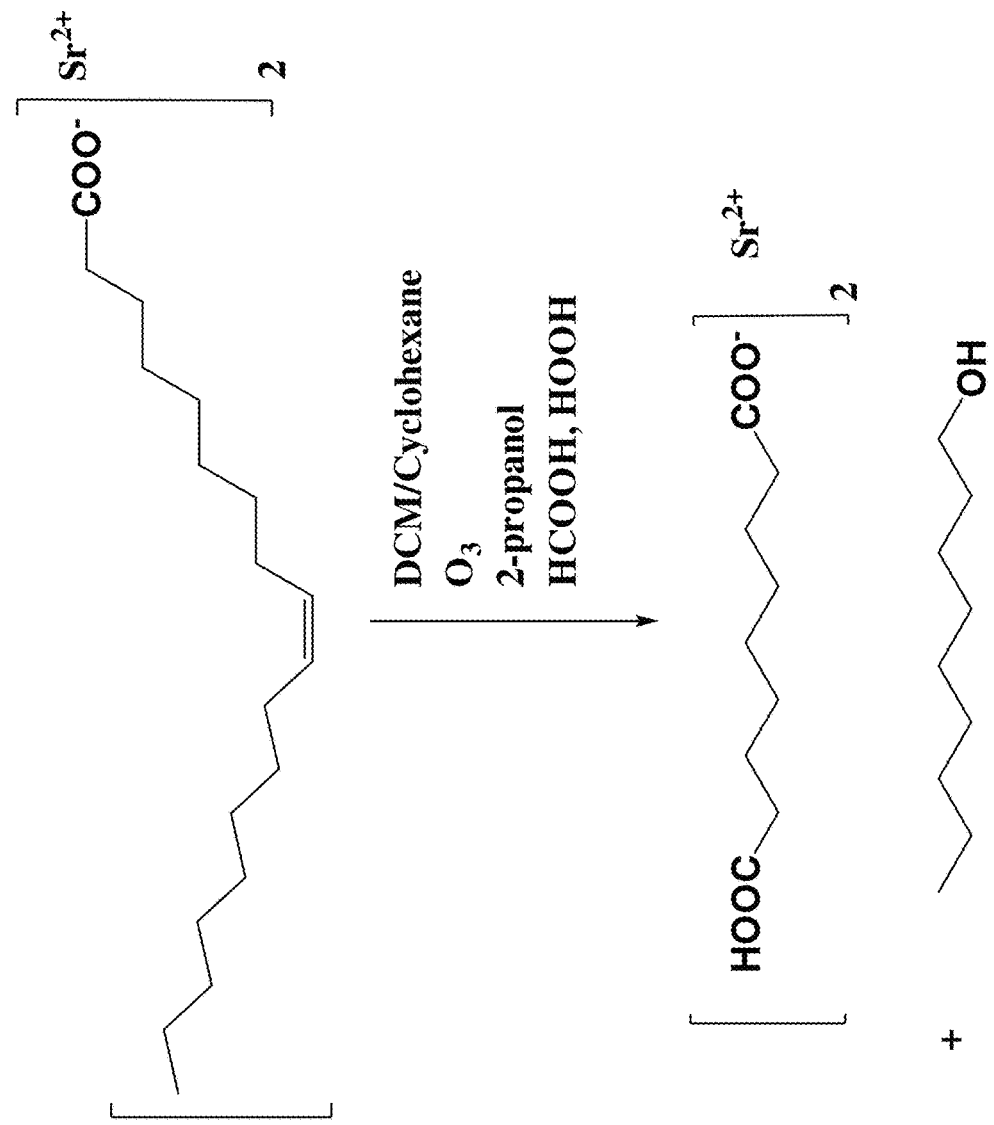
FIG. 2 illustrates functionalization of $SrF_2$ by treatment with an unsaturated carboxylic acid (oleic acid) and ozonolysis in dichoromethane (DCM) in the presence of 2-propanol, formic acid and hydrogen peroxide.
Figure 3:
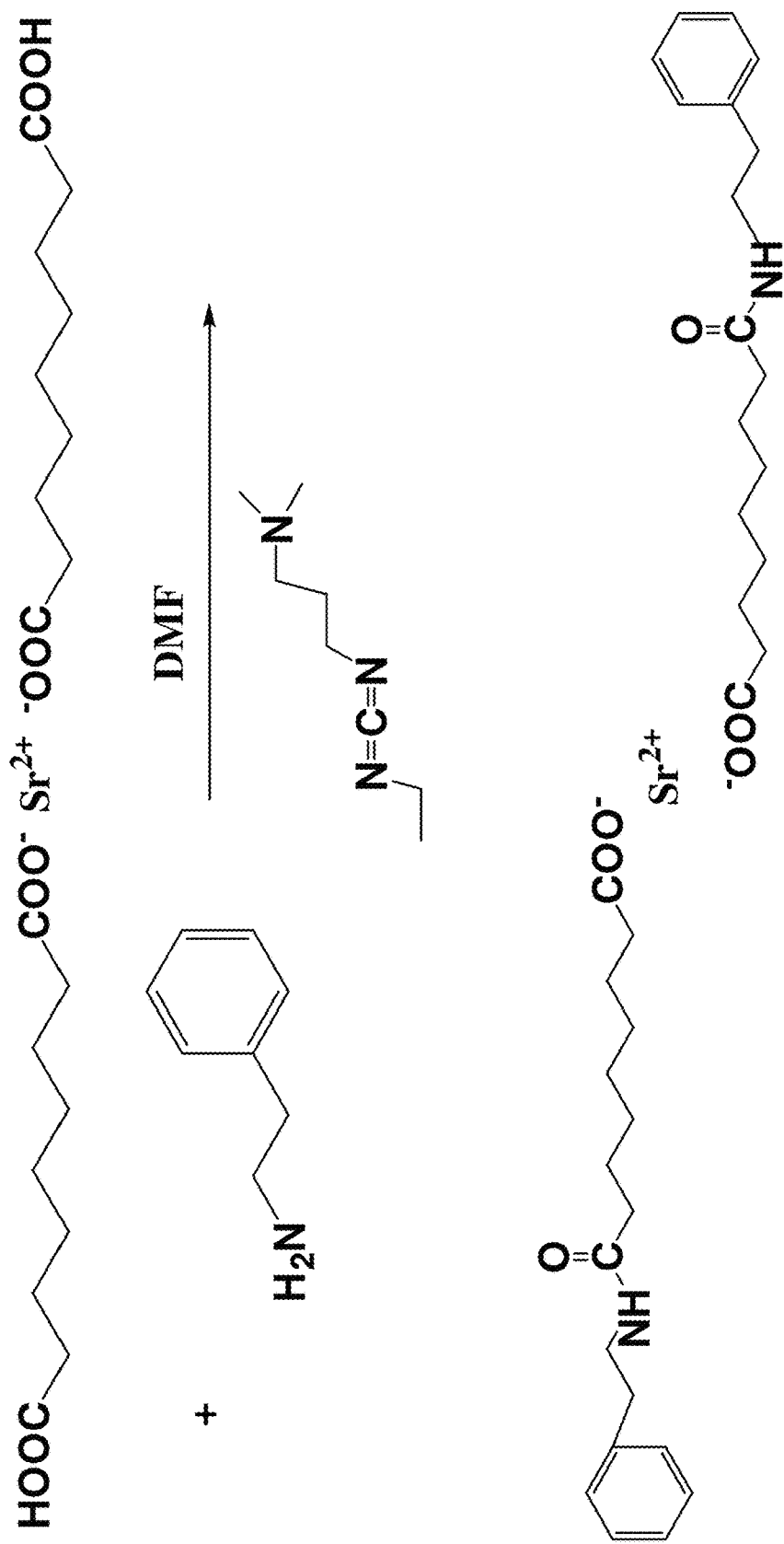
FIG. 3 illustrates amidation of the indicated Sr(2+) carboxylate via reaction of the identified carboxylic acid group with phenylethylamine in the presence of the indicated carbodiimide.

One preferred route for functionalization of the $SrF_2$ particles is illustrated in FIGS. 2 and 3. Experimental details are set out below.

Oleated Nanoparticles: Separate lots of strontium fluoride ($SrF_2$) nanoplatelets, nominally 0.7 g each, were produced as follows: Strontium nitrate aqueous solution (12 mL, 0.5 M), absolute ethanol (30 mL), oleic acid (30 mL) and sodium oleate (7.5 g) were combined in a conical centrifuge tube and sonicated for 10 minutes to form a transparent microemulsion. Hydrofluoric acid (12 mL, 1.0 M) was then added dropwise, and the resulting suspension was vortexed vigorously. Following transfer to a 125 mL PTFE-lined acid digestion vessel (Pan 4748), the suspension was heated to 180° C. for 72 h in a convection oven and then allowed to cool to room temperature over 8 h. Next, the solids were recovered from the separated suspension by centrifugation at 4800 rcf. The solids were resuspended in 50 mL cyclohexane, centrifuged, washed twice in 50 mL 80:20 cyclohexane/ethanol, and then resuspended in 100 mL cyclohexane.

Ozonolysis: A 2 L round-bottom flask was charged with a 1 L suspension of nanoplatelets in cyclohexane/dichloromethane. The suspension was chilled to −30° C. and stirred with a magnetic stirrer. Ozone was then introduced via a glass pipette tip at a nominal flow rate of 2 L/min. Ozone flow was continued for 30 minutes, yielding a dark-blue solution, and then stopped, after which the flask was sealed and allowed to warm slowly to room temperature. The ozonized suspension was then transferred to centrifuge bottles, centrifuged at 4000×g for 1 hr, and the solids redispersed in 350 mL 2-propanol.

After the removal of sample retains, a total of seven lots were combined in a 1 L round bottomed flask to give one batch with approximately 4.5 g solids in 250 mL cyclohexane suspension. An equivalent volume of dichloromethane was added to the round bottomed flask, and the resulting solution was chilled to −30° C. in a bath of acetone with added dry ice. Ozone was introduced to the solution at a rate of 2 L/min for 30 minutes, yielding a dark blue solution. The round bottomed flask was then purged with a gentle flow of nitrogen for 30 minutes, at which time the blue color had dissipated completely.

Oxidative Workup: The ozonized solids were isolated by centrifugation and redispersed into 200 mL isopropanol with sonication in a 1 L round bottomed flask. Formic acid (116 mL 88% aqueous solution) was then added to the stirred suspension, followed by hydrogen peroxide (14.2 mL, 30% aqueous solution) at room temperature. The resulting suspension was heated to 40° C. for 20 minutes, resulting in an exotherm of 10° C. Following a partial temperature drop (about 30 minutes later), the suspension was further heated to reflux for 1 h. The solution was allowed to cool passively, then the oxidized solids were then isolated by centrifugation, redispersed in 100 mL deionized water, frozen in liquid nitrogen, and lyophilized to dryness.

Amidation: A portion of the dried solids (3.4 g) was completely redispersed in 180 mL dimethylformamide with the aid of sonication. To the stifling suspension was added 80 mmol $RNH_2$ (R=Bz or phenethyl, Aldrich, 99.5%) followed by 80 mmol 1-ethyl-3-(3-dimethylaminopropyl)carbodiimide ("EDC", Fisher ACS grade), transferred by syringe. The suspension was stirred for five days at room temperature, resulting in a turbid suspension. The solids were isolated by centrifugation and redispersed in 250 mL dichloromethane, resulting in a nearly transparent suspension.

Analysis of $SrF_2$ Particles

The particle size of the above prepared $SrF_2$ particles was about 1.7 µm (largest linear dimension) with a polydispersity of 20% as measured by dynamic light scattering. Nevertheless, the electrophoretic mobility remained relatively high in acetonitrile and quite acceptable in dichloromethane with the particles having a net negative zeta potential. The zeta potential for the phenethylamidated $SrF_2$ (FIG. 3) was −25.75+/−0.52 mV as measured in acetonitrile (ZetaPALS 90 Plus instrument, Brookhaven Instrument Corp.) using a standard potential of 20 V, a field frequency of 2 Hz, and seven repetitions.

Figure 4:
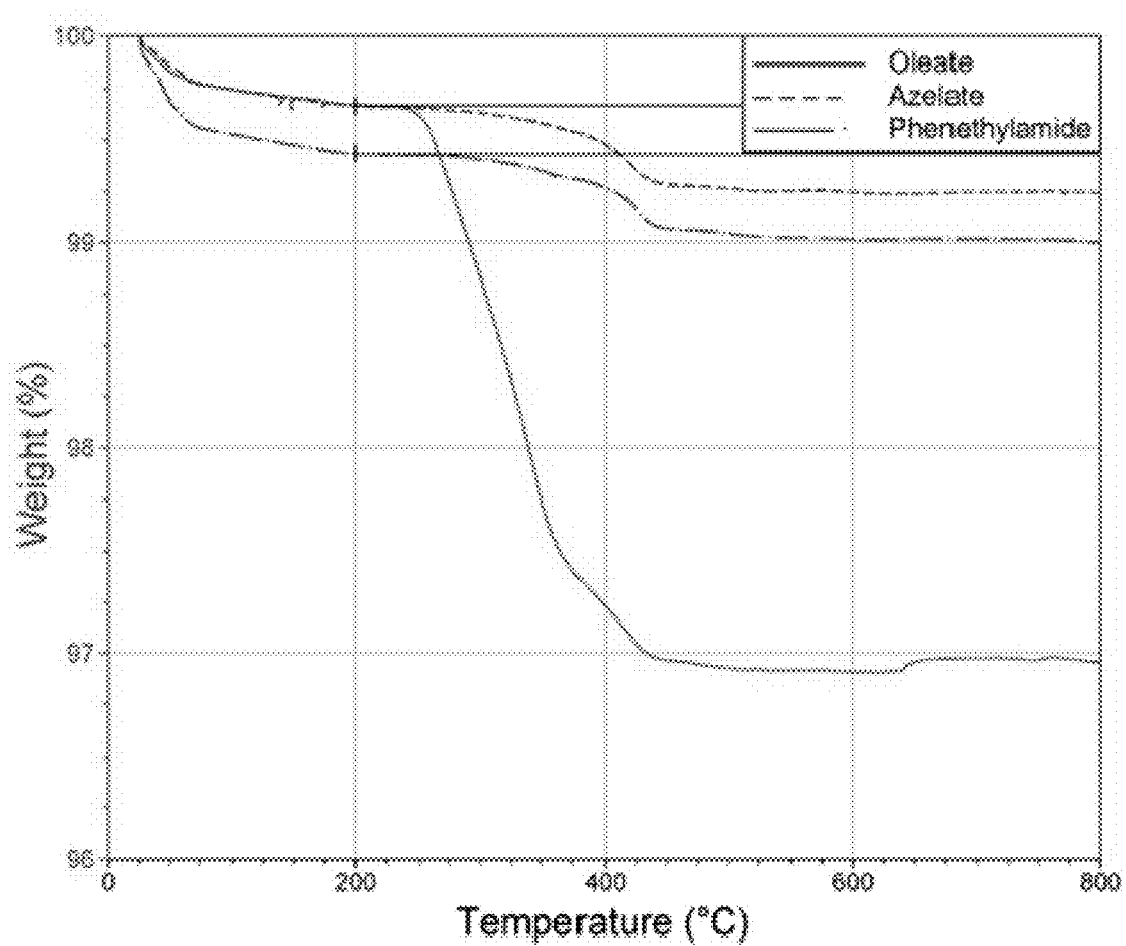
FIG. 4 shows a thermogravimetric analysis (TGA) of variously functionalized strontium fluoride ($SrF_2$) nanoplatelets (oleate, azelate, phenylethyl amide)
Figure 5:
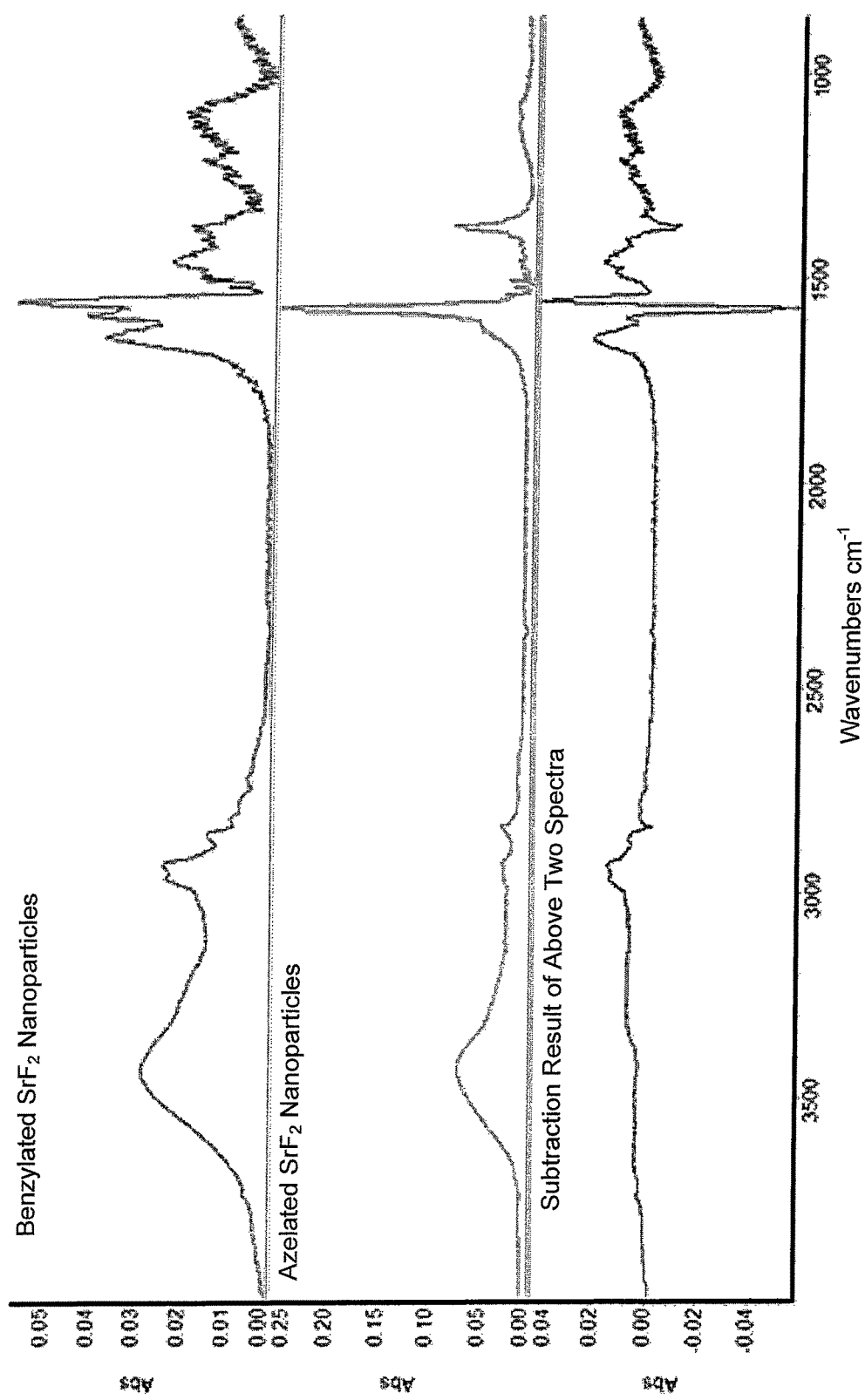
FIG. 5 shows a fourier-transform infrared spectrometry (FTIR) spectra of benzylamide and azelaic acid terminated $SrF_2$ nanoparticles and the subtraction spectra showing evidence of the amidization reaction.
Figure 6:
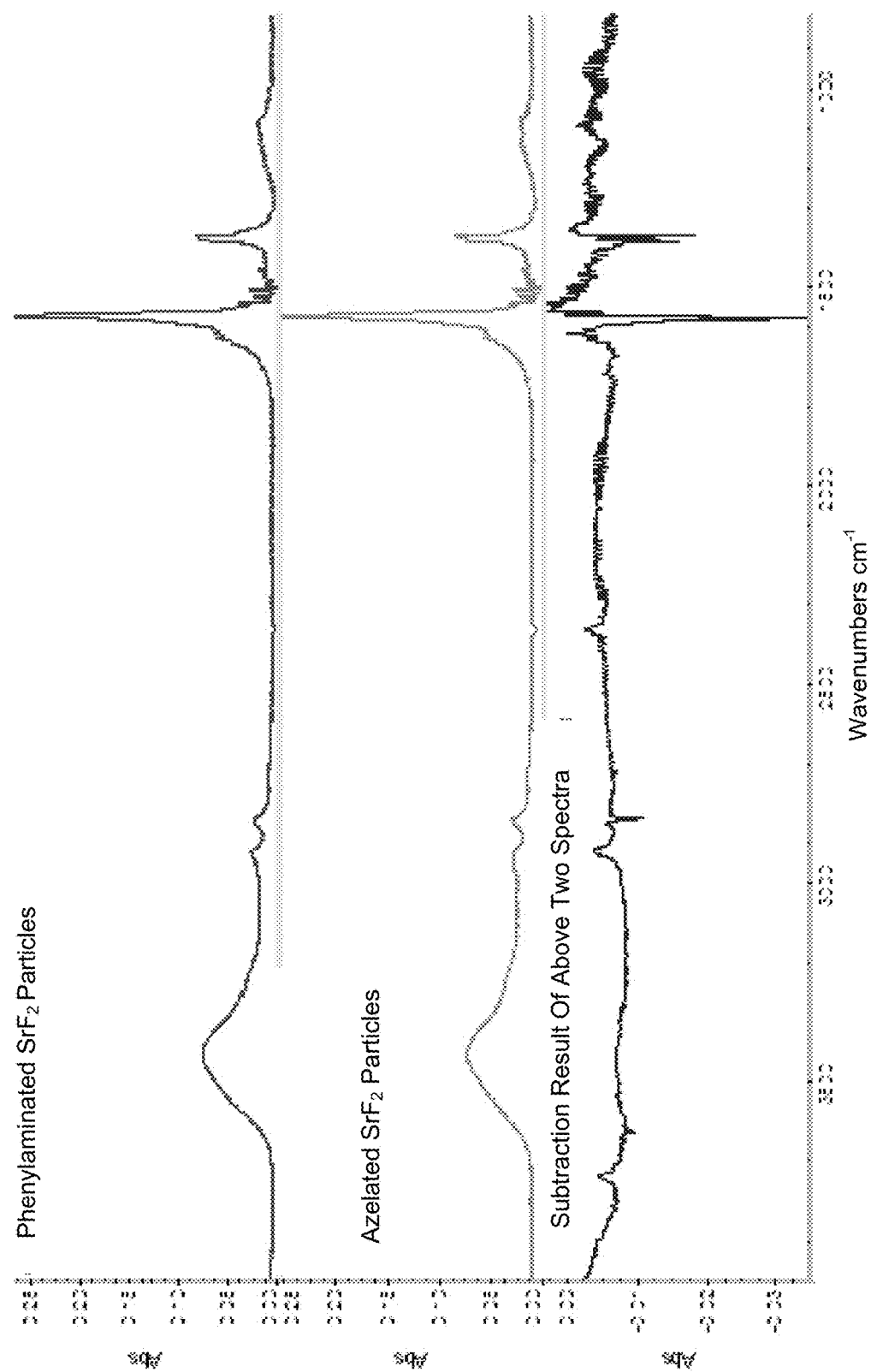
FIG. 6 shows a fourier-transform infrared spectrometry (FTIR) spectra of phenylethylaminated, azelaic acid terminated $SrF_2$ nanoparticles and the subtraction spectra showing evidence of the amidization reaction.

Thermogravimetric analysis (TGA) was conducted on a SDT Q-600 from TA Instruments. TGA samples were heated at a rate of 20° C./min in alumina crucibles, under a purge of dry air (10 $cm^3$/min), over the range of 25-800° C. See FIG. 4. Although the oleate functionalized nanoplatelets consisted of about 3 wt % organic (multilayer coating), less than 1 wt % organic was seen for the phenylethylamide, benzylamine and azelate functionalized nanoplatelets suggesting a thin monolayer coating Fourier-transform infrared spectrometry (FTIR) was conducted using a Magna-IR 560 spectrophotometer (Thermo Nicolet, Madison, Wis.) operated in transmission mode. Sample pellets were prepared by grinding the specimen together with KBr and compacting the powder with a hydraulic press. Even though the oleate functioned nanoparticles did not show a tendency to absorb water the phenylethyamide, benzylamide, and azelaic acid functionalized platelets all were hydroscopic (3400 $cm^{-1}$) (FIGS. 5 and 6). In order to determine the extent of amidization a spectral subtraction between the azelated and amidated particles was performed as illustrated. Amidation was conducted using benzyl amine and phenyl ethyl amine. The subtraction spectra showed that significant amidization had taken place. In addition the spectral changes were similar for both phenyl ethyl and benzyl functionalization considering the difference of only one $CH_2$ group. Accordingly, amidization was sufficient to permit suspension of the azelaic acid functionalized strontium fluoride ($SrF_2$) in methylene chloride which was employed to promote subsequent EPD co-deposition with a PLGA matrix polymer.

Hydrophobic Polymers for Co-EPD

As noted above, the $SrF_2$ particles herein may be employed along with a hydrophobic polymer for co-electrophoretic deposition (application of an electrical potential and deposition of a coating or self-supporting film on a metallic substrate). The hydrophobic polymers are preferably those that are non-water soluble and have a ζ-potential of zero. Such hydrophobic polymers preferably include the ability to form an anionic end group which may then form an ionic associationg with the $Si^{2+}$ ion available from the $SrF_2$ nanoparticles. As noted above, the hydrophobic polymers may therefore include hydrocarbon functionality as in the formula $CH_3(CH_2)_n$-A where n has a value of 5-50 and A is selected from a carboxylic acid group (—COOH), thiol group (—SH), and/or hydroxy group (—OH) or ester group —COOR', where R' may be an alkyl or aromatic group.

A preferred polymer herein includes poly(lactic-co-glycolic acid) or PLGA which is further capable of biodegradation via hydrolysis of its ester linkages. In addition, with respect to the use of PLGA, one may vary the lactic acid to glycolic acid ratio and/or the tacticity of the polylactic polymer to produce either an amorphous or semicrystalline deposited polymer matrix for the $SrF_2$ particles. For example, one may employ block copolymers that are locally isotactic. Isotactic poly-L-lactide can provide crystallinity of around 40%. It is also contemplated herein that one may utilize polylactic acid or polyglycolic acid in copolymer form, where the copolymer includes polyethylene oxide or polycaprolactone. Accordingly, one may form a polylactic acid-polyethylene oxide copolymer and/or a polyglycolic acid-polyethylene oxide copolymer.

EPD of $SrF_2$ Nanoparticle Loaded Composites

Figure 7:
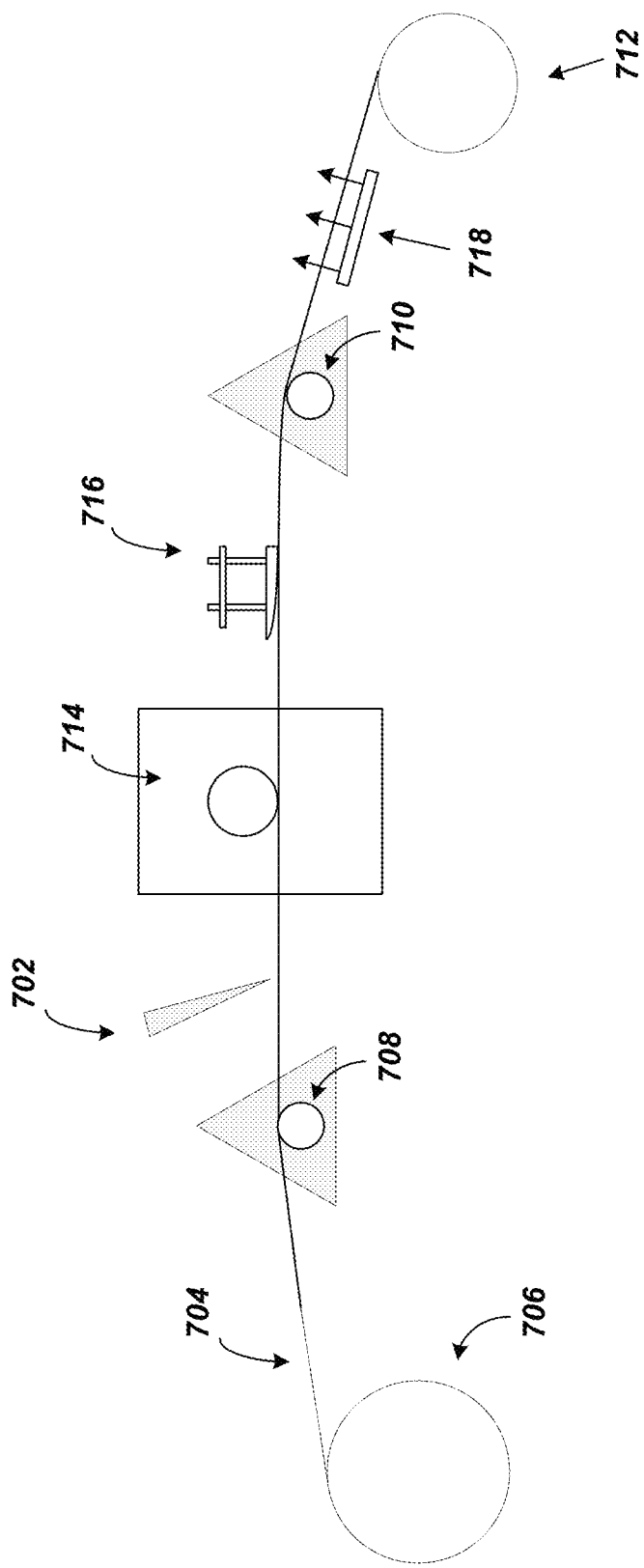
FIG. 7 shows a continuous electrophoretic deposition (EPD) apparatus.
Figure 8:
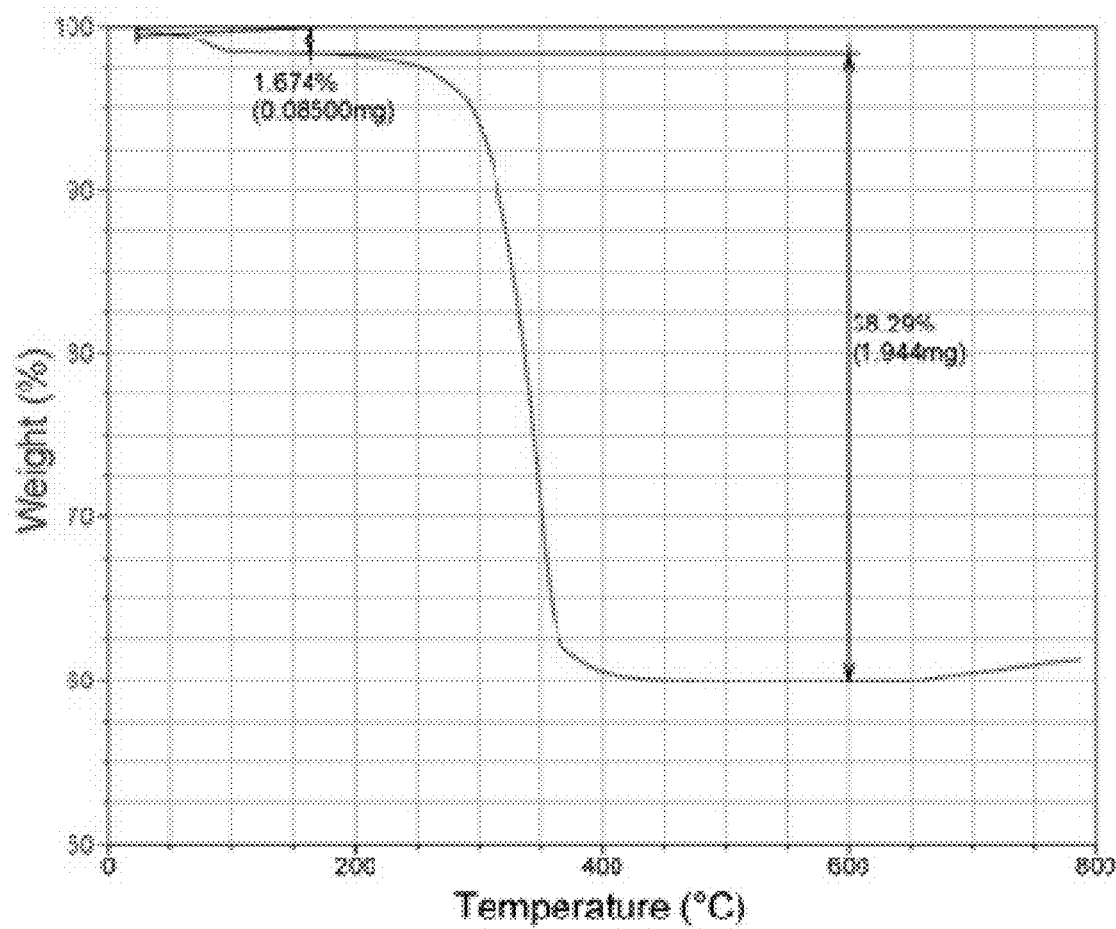
FIG. 8 shows a thermogravimetric analysis TGA depicting burnout of organic fraction for an EPD deposited phenylethylamide/azelaic acid functionalized $SrF_2$/PLGA composite. Using $\rho^{SrF2}$=4.24 g/cc and $\rho^{PLGA}$=1.29 g/cc, the volume fraction of $SrF_2$=0.32.

A flexible design for co-EPD deposition on a stainless steel strip was constructed and is shown in FIG. 7. The process is as follows: a relatively viscous polymer suspension containing the aforementioned nanoparticles of $SrF_2$ along with a hydrophobic polymer (e.g. PLGA), having an overall viscosity in the range of 1-2000 cP, is injected through a slot nozzle 702 onto a conductive stainless steel metal foil 704 (nominally 1.5" wide). The metal foil 704 will therefore serve as a counterelectrode. A feed roller is shown at 706 along with adjustable guide rollers at 708 and 710 and take-up roller 712. Next, the viscous suspension is flattened and shear-aligned by a PTFE roller 714 with a variable rate of rotation. Immediately following the roller, a charged floating plate 716 applies the required electric field for co-EPD. The electric field can be in the range of 5V/cm to 5 kV/cm. Then, the solvent is flashed away by a heated blower 718 and the dried tape is collected on a takeup spool 712.

The solvents suitable for co-EPD herein are selected from aprotic type solvents. This therefore includes, but is not limited to, solvents that do not donate hydrogen ($H^+$). This therefore includes, but is not limited to, tetrahydrofuran, methyltetrahydrofuran, methylene chloride, ethyl acetate, dimethyformamide, acetonitrile and dimethylsulfoxide. The overall concentration of solids (functionalized $SrF_2$ nanoparticles) in the aprotic solvent may be in the range of 0.5-20%. More preferably, the solids concentration may be in the range of 1-5%.

Preferably, the weight percent of $SrF_2$ particles and the subject hydrophobic polymer after deposition (coating or self-supporting film) may be in the range of 35%-90% by weight, with the corresponding amount of hydrophobic polymer falling in the range of 65%-10% by weight.

In one preferred version a relatively thin fluorocarbon film at a thickness of 14 Angstroms can be placed onto the metal surface to permit subsequent detachment of the $SrF_2$/polymer composite as the self-supporting film from a stainless steel substrate. The self-supporting films may have a thickness of 1.0-50 µm. This self-supporting film can then be spirally wrapped to the desired thickness. Accordingly, 1-10 layers of film may be applied around a given IM rod section prior to insertion. Then, the film may be heated to a temperature sufficient to fuse the polymer to create a strong interlayer and composite-metal bond which would survive insertion. Such temperature for fusing may be at or above the Tg or at or above the Tm of the polymer component. In a second version the substrate could be a biodegradable Mg alloy and the $SrF_2$/polymer self-supporting film could be wrapped around the IM nail.

The EPD conditions suitable for production of the partially amidated, azelated $SrF_2$/PLGA on electrically conductive ITO (indium tin oxide) coated glass slides was explored. Initially, PLGA (ester terminated, lactide:glycolide 85:15, $M_w$=50,000-75,000, Aldrich) was combined with the $SrF_2$ nanoparticles at a mass ratio of 2:1 and an overall concentration of 2% solids in dichloromethane as the suspension medium. Particle deposition was controllable in dichloromethane, and the polymer-particle ratio could be tailored by changing the applied DC potential. Due to the high particle mobility, it proved very easy to deposit a uniform nanoparticle film with 5% (w/w) PLGA matrix at 100 V/cm. The films were self-limiting in thickness due to the insulating characteristics of the deposited film, and the composition remained consistent over several depositions despite depletion of the particle suspension. That is, there appeared to be a thickness for each polymer/nanoparticle system at which the deposited film was insulating rather than dielectric. At that point no further potential exists and the film ceases to grow thicker. Swollen films may be 2-3 mm thick. Following solvent evaporation, film thickness can fall in the range of 10-100 microns.

Thus, the film composition is relatively more dependent upon particle mobility than on particle concentration. Significant control over the film composition derived from dichloromethane by reducing the applied EPD potential to 20 V/cm has been achieved. The films, which contain approximately 32% (v/v) $SrF_2$ (via TGA data shown in FIG. 8) or 60% (w/w) $SrF_2$, are optically translucent and tenaciously adherent to an indium tin oxide substrate. These films were employed for subsequent mechanical analysis (pin on disk, elastic modulus, wear).

Mechanical Properties of $SrF_2$/Polymer Composites

The surface morphology of EPD deposited $SrF_2$/polymer composites were imaged with Scanning electron microscopy (SEM) using an EVO 50EP microscope (Carl Zeiss SMT, Germany) equipped with extended pressure capabilities, a backscattered electron (BSE) detector, a variable pressure secondary electron (VPSE) detector, and a scanning transmission electron (STEM) detector and operated at 20 kV. Samples were gold decorated (ca 10 Angstrom Au particles) prior to imaging to improve sample conductivity.

Figure 9:
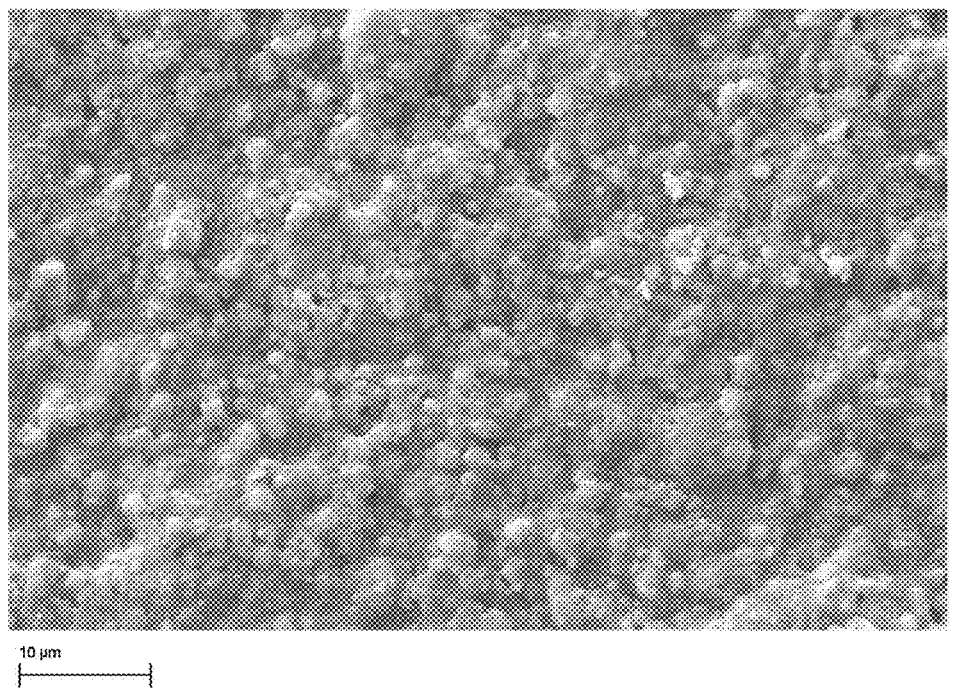
FIG. 9 shows an environmental scanning electron microscope (ESEM) image of EPD deposited film (same composition as in FIG. 7). 20V/cm-ca. 40 wt % PLGA/60 wt % $SrF_2$.
Figure 10:
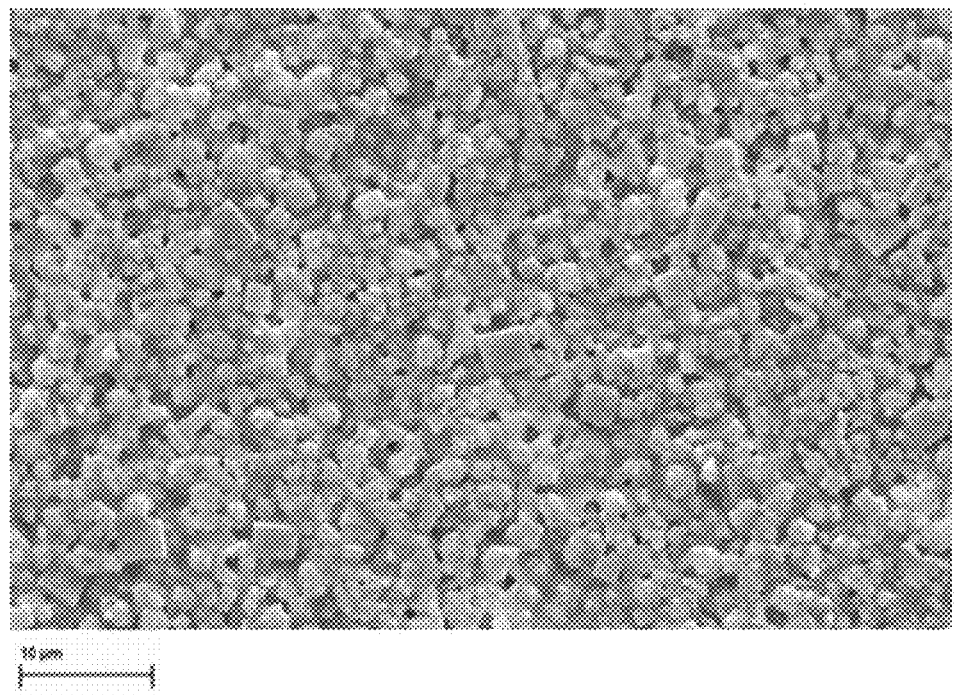
FIG. 10 shows an environmental scanning electron microscope (ESEM) image of EPD deposited $SrF_2$ nanoplatelet/ PLGA film with 5% (w/w) matrix PLGA polymer showing broad platelet size distribution. The film is remarkably dense due to interstitial filling by the smaller particles. 100V/cm-ca.5 wt % PLGA/95 wt % $SrF_2$.

FIG. 9 shows the typical surface morphology of a 2-3µ thick EPD composite with surface roughness induced by $SrF_2$ coated by PLGA (32% (v/v) $SrF_2$ or 60% (w/w) $SrF_2$. A similar PLGA film is featureless at this magnification. FIG. 10 shows an EPD composite with much lower PLGA content (95% w/w inorganic) exposing the nanoparticle morphology more clearly.

In the next set of experiments a pin on disk instrument was used to measure the elastic modulus, hardness of the film at 25° C. in FIG. 9. A Hysitron Nanoindentor using a cube corner tip at tip forces between 750-500 µN was employed. Each indent had a 5 second load, 2 second dwell, and a 5 second unload. The film demonstrated an elastic modulus calculated according to the instrument software of 26.9±0.75 GPa considerably in excess of that measured for the neat spun coated PLGA film (6.87±0.25 GPa) of about 1µ thickness. The probe penetration depths for the case of the composite film were between 0.57 and 0.25µ so the registered modulus value was accurate. On the other hand the probe penetration depth in the PLGA film was ca 0.7µ, a substantial percentage of the entire film thickness, suggesting that the modulus of the glass substrate (ca E=50 GPa) was probably contributing. The Young's modulus of this type of PLGA is typically in the range of 2.8 GPa, $T_g$=45° C. Thus the results reveal that the composite film was significantly hardened at $SrF_2$ volume fractions of 0.32. The Young's modulus of single crystal $SrF_2$ at RT is 90 GPa. Accordingly, the elastic modulus of the $SrF_2$/hydrophobic polymer films formed via co-EPD will fall in the range of 45-85 GPA.

Figure 11A:
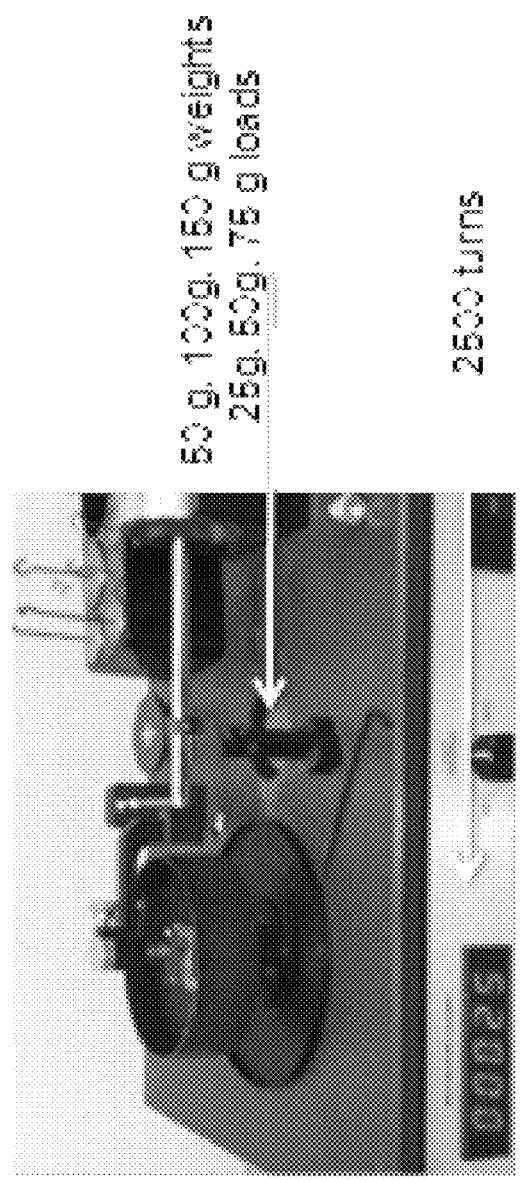
FIG. 11A shows a test apparatus comprising a pin located on a disk to conduct wear testing experiments.
Figure 11A:
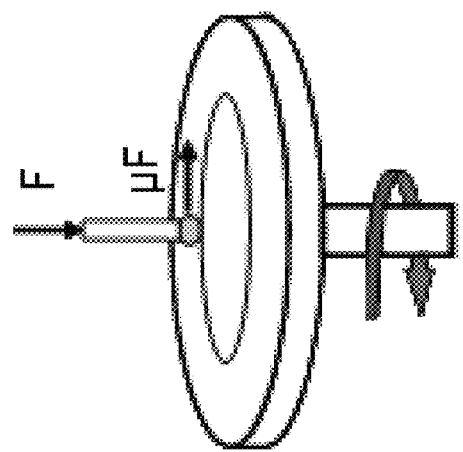
Figure 11B:
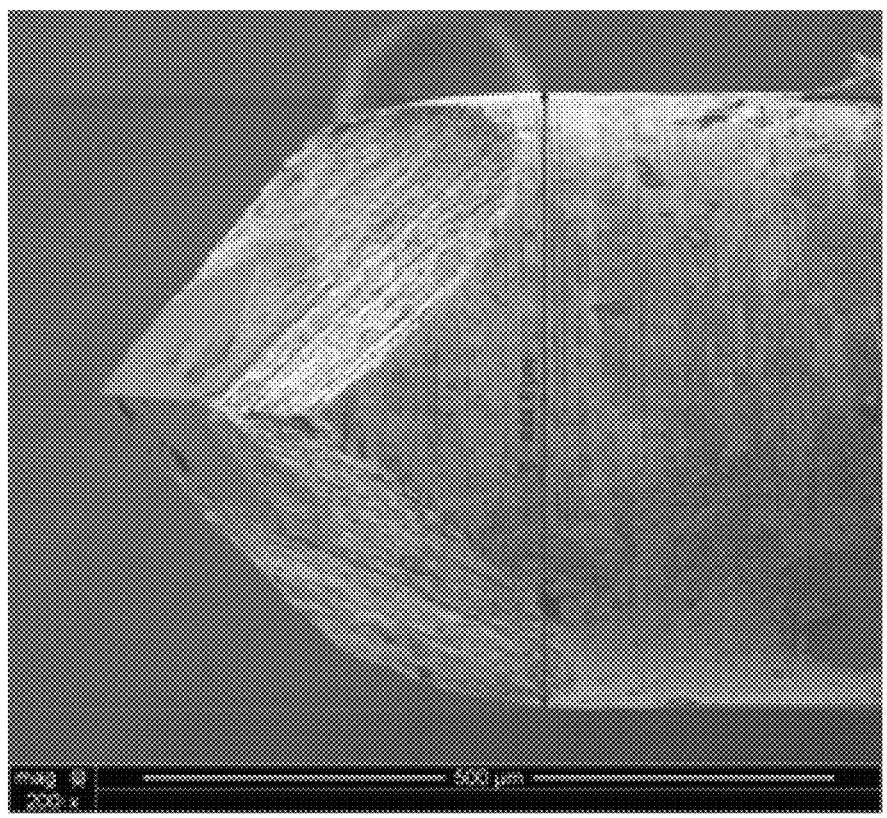
FIG. 11B shows the indentation probe used for the wear test apparatus of FIG. 10A.

The composite film represented in FIG. 9 was wear tested using a hard spherical pin of 0.25 diameter (6350µ) using the apparatus shown in FIG. 11A. Loads of 25 g, 50 g, and 75 g were employed for room temperature testing. The shape of the nanoindenter probe from the previous experiment is also included in FIG. 11B. The coefficient of friction µ over the same path length (outer circle 75 g load, middle circle 50 g load, inner circle 25 g load) is shown in FIG. 12. All µ show a fast increase from µ=0.3 to 0.4 and then a slow increase to 0.5 or 0.58 for the highest load. The uncoated base glass substrate µ quickly levels out at 0.7. The µ for the neat PLGA films levels out at ca. 0.45. Thus, it appears that the $SrF_2$/polymer composite exhibits a frictional behavior intermediate between the glass substrate and PLGA. Preferably, the coefficient of friction for the films or coatings is at or below 0.6

The profilometer image and wear track for the same sample is shown in FIGS. 12 and 12B for the 50 m travel in the track (ca. 400µ wide, more than one order of magnitude smaller than the indenter ball diameter). As expected from the ESEM results the profilometer measures the surface roughness at ca. 0.5µ. ESEM photographs of the same sample are shown at various magnifications in FIGS. 13A 13B, 14A, 14B, 15A and 15B.

At a load of 25 g it appears that a PLGA smear layer forms in the track with minimal $SrF_2$ nanoparticle/polymer fracture; at intermediate load of 50 g the smear layer starts to fragment, and finally at the highest load of 75 g the track is almost completely ablated down to the glass substrate surface where the friction coefficient starts to rise toward the substrate glass level. At the highest loads one can easily observe individual $SrF_2$ nanoparticle clusters that have fractured from the matrix polymer and the smooth glass substrate underneath.

One unexpected observation is that a relatively small load actually reduces the surface roughness of the electrophoretically deposited $SrF_2$ nanoparticle/polymer coating herein. It is contemplated that this may be due to yielding of the PLGA matrix and impression of the protruding $SrF_2$ particles into the film. This process also occurs at relatively higher loads but with ablation which may be due to tearing of coating from the underlying substrate surface.

Accordingly, it may now be appreciated that the present invention provides for the deposition of a coating or film of organ-functionalized $SrF_2$ nanoparticles that may be applied to a medical device via electrophoretic deposition that is suitable for implantation in a human or animal. The medical device may therefore comprise a metallic substrate such as Ti, Mg or stainless steel which may be in the form of intramedullary rods or implant plates. The coatings or films have been found to have substantial abrasion resistance that withstands surgical insertion. In addition, the coatings or films may provide controlled release of $Sr^{2+}$ to assist in bone healing. In addition, the coatings or films herein can release F which then will improve the mechanical properties of the bone calcium phosphate.

It is noted that the spacio-temporal concentration of $Sr^{2+}$ and F in the vicinity of the coated implant would depend upon the biodegradation rate of the PLGA polymer matrix and dissolution rate of the $SrF_2$ nanocrystals assisted by chelation of $Sr^{2+}$ by lactic and glycolic acid biodegradation products and characteristics of local circulation and protein/mineral deposition on the implant. All of these factors would affect absorption into local tissue to activate the anabolic-anticatabolic processes. Accordingly, it can be appreciated that the films or coatings herein now provide sufficient flexibility in the deposition system so that release rates of the indicated ions can be readily adjusted to maximize the release in vivo.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

What is claimed is:

1. A method for forming a $SrF_2$ particle/polymer coating or self-supporting film on a metallic cathode comprising:
    (a) supplying particles of $SrF_2$ capable of providing $Sr^{2+}$ ions wherein said particles have a largest linear dimension of 20 nm to 10.0 μm;
    (b) supplying a hydrophobic polymer and forming an ionic association between said hydrophobic polymer and said $Sr^{2+}$ ions of said $SrF_2$ particles, wherein said hydrophobic polymer comprises polylactic acid, polyglycolic acid, poly(lactic-co-glycolic acid), co-polymers of polylactic acid, or co-polymers of polyglycolic acid, wherein said co-polymers include polycaprolactone;
    (c) placing said $SrF_2$ particles that are ionically associated with said hydrophobic polymer in an aprotic solvent, wherein said aprotic solvent is selected from the group consisting of tetrahydrofuran, methyltetrahydrofuran, ethyl acetate, dimethylformamide, acetonitrile, dimethylsulfoxide and dichloromethane, and applying a potential in the range of 5 V/cm to 5 kV/cm between a charged plate in said aprotic solvent and said metallic cathode and depositing a coating or self-supporting film containing $SrF_2$ particles that are ionically associated with said hydrophobic polymer on said metallic cathode, wherein said metallic cathode is a stainless steel substrate or a degradable Mg alloy;
    (d) removing said coating or self-supporting film containing $SrF_2$ particles from said metallic cathode;
    (e) wrapping said coating or self-supporting film containing $SrF_2$ particles around a metal implant; and
    (f) heating said coating or self-supporting film containing $SrF_2$ particles at a temperature above the Tg of the hydrophobic polymer or above the Tm of the hydrophobic polymer and fusing said hydrophobic polymer.

2. The method of claim 1 wherein said coating or self-supporting film contains $SrF_2$ at a level of 35-90% by weight and said hydrophobic polymer at a level of 65%-5% by weight.

3. The method of claim 1 wherein said metal implant is an intramedullary nail for implantation in a human or animal.

4. The method of claim 1, wherein said $SrF_2$ particles have a geometry that exhibits a thickness in the range of 1 nm to 200 nm.

5. The method of claim 1, further comprising preparing said $SrF_2$ particles by hydrothermal synthesis, wherein the $SrF_2$ particles are crystallized from a solution.

6. The method of claim 1, further comprising applying a fluorocarbon film onto the metallic cathode before depositing said coating on said metallic cathode, wherein said metallic cathode is formed from stainless steel.

7. The method of claim 1, wherein said $SrF_2$ particles are phenethylamidated $SrF_2$ particles and exhibit a zeta potential of −25.75+/−0.52 mV, wherein said zeta potential is measured in acetonitrile, using a standard potential of 20 V, a field frequency of 2 Hz and seven repetitions.

8. A method for forming a $SrF_2$ particle/polymer coating on a metallic cathode comprising:
    (a) supplying particles of $SrF_2$ capable of providing $Sr^{2+}$ ions wherein said particles have a largest linear dimension of 20 nm to 10.0 μm;
    (b) supplying a hydrophobic polymer and forming an ionic association between said hydrophobic polymer and said $Sr^{2+}$ ions of said $SrF_2$ particles, wherein said hydrophobic polymer comprises a hydrocarbon polymer having the formula $CH_3(CH_2)n\text{-}A$ wherein n has a value of 5-50 and A is carboxylic acid (—COOH);
    (c) placing said $SrF_2$ particles that are ionically associated with said hydrophobic polymer in an aprotic solvent, wherein said aprotic solvent is selected from the group consisting of tetrahydrofuran, methyltetrahydrofuran, ethyl acetate, dimethylformamide, acetonitrile, dimethylsulfoxide and dichloromethane, and applying a potential in the range of 5 V/cm to 5 kV/cm between a charged plate in said aprotic solvent and said metallic cathode and depositing a coating containing $SrF_2$ particles that are ionically associated with said hydrophobic polymer on said metallic cathode.

9. The method of claim 8 wherein said hydrophobic polymer having the formula $CH_3(CH_2)n\text{-}A$ comprises oleic acid which forms the following ionic association with $Sr^{2+}$ of said $SrF_2$ particles:

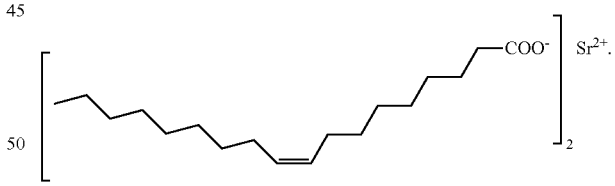

10. The method of claim 9 further comprising the step of said ionic association of oleic acid with said $SrF_2$ particles undergoing ozonolysis and treatment with an organic alcohol, an organic acid and a peroxide and being converted to:

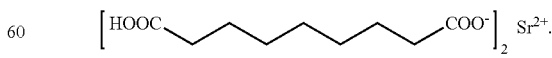

11. The method of claim 10 wherein the carboxylic acid groups are converted to amide groups.

* * * * *